(12) United States Patent
Manetakis et al.

(10) Patent No.: US 7,179,265 B2
(45) Date of Patent: Feb. 20, 2007

(54) REDUCED DIAMETER CLIP APPLYING ARRANGEMENT

(75) Inventors: Emmanuel Manetakis, Burlington, MA (US); Henri F. DeGuillebon, Manchester/Sea, MA (US); Ly Ung, Swampscott, MA (US)

(73) Assignee: Microline PENTAX, Inc., Beverly, MA (US)

( * ) Notice: Subject to any disclaimer, the term of this patent is extended or adjusted under 35 U.S.C. 154(b) by 562 days.

(21) Appl. No.: 10/457,324

(22) Filed: Jun. 9, 2003

(65) Prior Publication Data

US 2004/0010272 A1    Jan. 15, 2004

Related U.S. Application Data

(63) Continuation-in-part of application No. 10/085,737, filed on Feb. 28, 2002, now Pat. No. 6,840,945, and a continuation-in-part of application No. 10/158,726, filed on May 30, 2002, now Pat. No. 6,911,033.

(51) Int. Cl.
*A61B 17/10* (2006.01)

(52) U.S. Cl. ........................ 606/142; 606/143

(58) Field of Classification Search ............... 606/139, 606/142, 143, 219, 221, 151, 157, 158
See application file for complete search history.

(56) References Cited

U.S. PATENT DOCUMENTS

| | | | |
|---|---|---|---|
| 3,638,847 A | 2/1972 | Noiles et al. | |
| 4,522,207 A | 6/1985 | Klieman et al. | |
| 4,637,395 A * | 1/1987 | Caspar et al. | ................ 606/143 |
| 4,674,504 A | 6/1987 | Klieman et al. | |
| 4,892,244 A | 1/1990 | Fox et al. | |
| 5,174,300 A | 12/1992 | Bales et al. | |
| 5,246,450 A | 9/1993 | Thornton et al. | |
| 5,483,952 A | 1/1996 | Aranyi | |
| 5,607,436 A | 3/1997 | Pratt et al. | |
| 5,626,585 A | 5/1997 | Mittelstadt et al. | |
| 5,626,608 A | 5/1997 | Cuny et al. | |
| 5,772,673 A | 6/1998 | Cuny et al. | |
| 5,951,577 A | 9/1999 | Mayenberger et al. | |
| RE36,720 E | 5/2000 | Green et al. | |
| 6,059,799 A | 5/2000 | Aranyi et al. | |
| 6,277,131 B1 | 8/2001 | Kalikow | |
| 6,306,149 B1 | 10/2001 | Meade | |
| 6,599,298 B1 | 7/2003 | Forster et al. | |
| 6,679,894 B2 * | 1/2004 | Damarati | ................ 606/143 |

* cited by examiner

*Primary Examiner*—Julian W. Woo
(74) *Attorney, Agent, or Firm*—Greenblum & Bernstein, P.L.C.

(57) ABSTRACT

A clip applying device for the insertion and pinching of a medical clip within a mammalian body portion. The device comprises a housing supporting a proximal end of a delivery tube of the device. A pair of pinchable jaws are movably arranged at a distal end of the delivery tube. The device contains a plurality of preformed clips of a first width, the clips having leg portions, the clips also being movably disposed within the delivery tube between the housing and the jaws. A tool adjacent the jaws is arranged to enlarge the clips from a first width to a wider second width, as the clips emerge from the delivery tube.

24 Claims, 8 Drawing Sheets

REDUCED DIAMETER CLIP APPLYING ARRANGEMENT

The present invention is a continuation-in-part application of U.S. patent application Ser. Nos. 10/085,737, filed 28 Feb. 2002 now U.S. Pat. No. 6,840,945, and 10/158,726 filed 30 May 2002 now U.S. Pat. No. 6,911,033 which are each incorporated herein by reference in their entirety.

BACKGROUND OF THE INVENTION

1. Field of the Invention

The present invention relates to clip applying devices for medical uses and more particularly to a medical clip applying device of reduced diameter of five millimeters in barrel diameter.

2. Prior Art

Medical clips are utilized in countless operations within the human body. In the field of laparoscopic surgery, the goal is to provide patient healing with minimal injury to that patient during an operative procedure. Medical clip applying devices are utilized to pinch and seal tissue during that operative procedure. Such clip applying devices have elongated barrels which are disposed through openings in the human body so as to place and subsequently pinch those clips therewithin. Typically the barrels of those clip applying devices are about ten millimeters in diameter. Reducing the size of the barrel would minimize the size of the opening within the body tissue being pierced and would thus promote faster healing of the patient.

It is the object of the present invention, to overcome the disadvantages of the prior art.

It is yet a further object of the present invention to provide a clip applying device with a narrower tubular barrel than exists in the current prior art.

It is an object of the present invention to provide a clip applying device whose tissue binding clips have "effective" dimensions which correspond to clip applier standard ten millimeter dimension yet their delivery arrangement is half that size otherwise required.

It is still yet further another object of the present invention to provide a medical clip applying apparatus having a clip whose entry is minimized yet whose effect once within the mammalian body is the same as a standard clip.

BRIEF SUMMARY OF THE INVENTION

The present invention relates to elongated medical clip applying devices having a first or proximal end and with a pistol like housing having a trigger therewith. A pistol like housing holds and feeds an elongated cylindrically shaped tube having a distalmost end. A plurality of clips are fed through the tube to a set of jaws at the distalmost end thereof. The clips are introduce to the jaws through a cartridge inserted at the proximal end of the pistol like housing at the proximal end of the clip applier arrangement, as may be seen in my earlier cited U.S. patent applications which are incorporated herein by reference in their entirety.

The clips of the present invention are fed through the barrel of the clip applying arrangement in a five millimeter cartridge instrument. Each cartridge, is similar to those shown in the aforementioned patent applications, except for their narrow dimensions of the present invention. The clips utilized in the medical clip applying arrangement of the present invention each comprise a pair of leg portions connected by a V-shaped bridging portion. As the clips reside and are pressed forward in the cartridge, they maintain a particular pre-formed configuration. That preformed configuration includes the legs being non-parallel, that is skewed at an angle of about 10 degrees with respect to their being parallel to one another, and their bridging portion defining a V of about 60–75 degrees. As the clips advance down towards the distal end of the cartridge, they are being pushed in a manner similar to that described in the aforementioned patent applications, they emerge from the distal end of the 5 millimeter tubular housing between the handle and the jaw portion of the medical clip applier arrangement.

An elongated forming tool is disposed immediately adjacent the jaws at the distal end of the 5 millimeter tube. The elongated forming tool includes a planar bracket portion having a distal end with a triangularly shaped forming tool thereon. The forming tool has an apex of one angle directed proximally towards the open end of the medical clips in the cartridge. The triangularly shaped forming tool has a pair of inclined surfaces which define the sides of the triangle and which engage the distalmost end of the pre-formed clips as they advance distally. As the preformed clips are each successively pushed distally, the sides of the triangle spread the legs apart while simultaneously somewhat straightening out the V-shaped bridging portion between those legs. The distal end of those legs of each successive clip are caused to enter a channel in each of the face portions of each respective jaw and are ready for pinching by those jaws around mammalian tissue within the human body. It is to be noted at this point that as the distal portion of the medical clip applier device is advanced into the abdominal area of a mammalian patient, those jaws are brought together to minimize their diameter and to keep them at that minimum diameter and in special conformance and alignment with the 5 millimeter tubular housing from which they extend. Once inside the patient, however, the jaws may be opened to receive the now spread apart leg portions of the newly formed (spread apart) clips within the body of the patient being operated upon.

Thus what has been shown is the utilization of a preformed clip having a leg spread diameter of no more than 5 millimeters being successively advanced along a feed cartridge within a 5 millimeter diameter barrel housing and upon emersion from the distal end of that housing, the legs of that pre-formed clip, going from a somewhat slightly pinched configuration and from its bridging portion being of a 75–90 degree V-configuration to a configuration where the legs are generally parallel by virtue of the bridging portion being somewhat straightened and thus spreading the width of those legs out to approximately 5.2 millimeters, which is generally the standard dimension of a standard prior art clip in a 10 millimeter tube of the prior art. Upon reaching the distalmost end of the track within the pinching jaws, those jaws are effected, to pinch together the clip along portions of a tissue to effect the pinched, clip's purpose. Withdrawal of the medical clip applying device is permitted, by the squeezing together of the jaws to the same overall diametric dimension as the elongated tubular housing enclosing the 5 millimeter cartridge which supplies the pre-formed clips therethrough.

Thus a narrow pre-formed clip of substandard dimensions is permitted to be delivered into a mammalian body and expanded within that mammalian body prior to its being pinched about tissue within that mammalian body by a narrow diameter delivery arrangement which thus minimizes the trauma to the patient and minimizes that patient's healing time.

The invention thus comprises a clip applying device for the insertion and pinching of a medical clip within a mammalian body portion, comprising: a housing supporting a proximal end of a delivery tube of the device; a pair of pinchable jaws movably arranged at a distal end of the delivery tube; a plurality of pre-formed clips of a first width, the clips having leg portions, the clips being movably disposed within the delivery tube between the housing and the jaws; and a tool adjacent said jaws arranged to enlarge the clips from the first width to a wider second width, as the clips emerge from the delivery tube. The tool may comprise a triangular form arranged to frictionally engage the leg portions of the clips to bias them apart. The clips have a pre-formed bridging portion connecting their leg portions, the bridging portion being of a "V" configuration. The leg portions may be skewed with respect to one another. The pre-formed bridging portion of the pre-formed clip of a first width, may preferably comprise an angle of about 75 to 90 degrees. The bridging portion of the clip of a second width, may preferably comprise an angle of about 90 to 110 degrees. The delivery tube may have an outer diameter of about 5 millimeters. The leg portions of the clip of a second dimension are parallel.

The invention may also comprise a method of introducing a medical clip into a mammalian patient, comprising the steps of: inserting an arrangement of clips of a first width dimension into a delivery tube, each of the clips having leg portions and a bridging portion between the legs, the delivery tube having a pair of clip pinching jaws on a distal end thereof; advancing the clips through the tube and towards the jaws after the delivery tube has been inserted into the patient; widening the clips into a second width dimension prior to pinching thereof; and squeezing each of the respective clips by the jaws when each successive clip is at the second width dimension, and about a tissue, to pinch that tissue, and serially forming the leg portions of each of the successive clips in a parallel relationship; engaging the leg portions of each of the clips by a forming tool so as to form the respective leg portions thereof into the parallel relationship; successively forming the bridging portion of each of the respective clips into a wider angled V shape; and squeezing the jaws together to permit the device to be removed from the patient through a 5 millimeter opening in the patient.

The invention may also comprise a method of introducing a narrow clip into a patient for pinching tissue within said patient comprising the steps of: introducing a delivery tube into a patient, the tube having a plurality of pre-formed clips of a narrow first width, aligned therein; widening the pre-formed clips to a second wider width upon advancement of said clips from the tube; pinching the clips by a pair of squeezable jaws arranged about tissue upon the clips being widened; and forming a bridging portion of the clip from about a 75 to 90 degree bend, preferably about 82 degrees therein into about a 90 to 110 degree bend, preferably about 100 degrees, to thus widen and spread apart the leg portions of the pre-formed clip.

The method invention may also include one or more of the following steps including: straightening a bridge portion of the clip by a forming tool prior to said pinching of the clip; sliding a distal end of each of a pair of legs of the clip on an edge of the forming tool to effect the straightening of the bridge portion of the clip; wherein the widening of the pre-formed clips comprises spreading leg members apart of the clip.

The invention may include a method of introducing a narrow clip into a patient for pinching tissue within the patient by a wider clip once within the patient, the method comprising the steps of: introducing a delivery tube into a patient, the tube having a plurality of pre-formed clips of a narrow first width, aligned therein; and widening the pre-formed clips to a second wider width upon advancement of the clips from the tube so as to be able to engage tissue and pinch the tissue with the widened clip; and the step of: pinching said widened clips within said patient.

BRIEF DESCRIPTION OF THE DRAWINGS

The objects and advantages of the present invention will become more apparent when viewed in conjunction with the following drawings, in which.

DETAILED DESCRIPTION OF THE PREFERRED EMBODIMENTS

Figure 1:
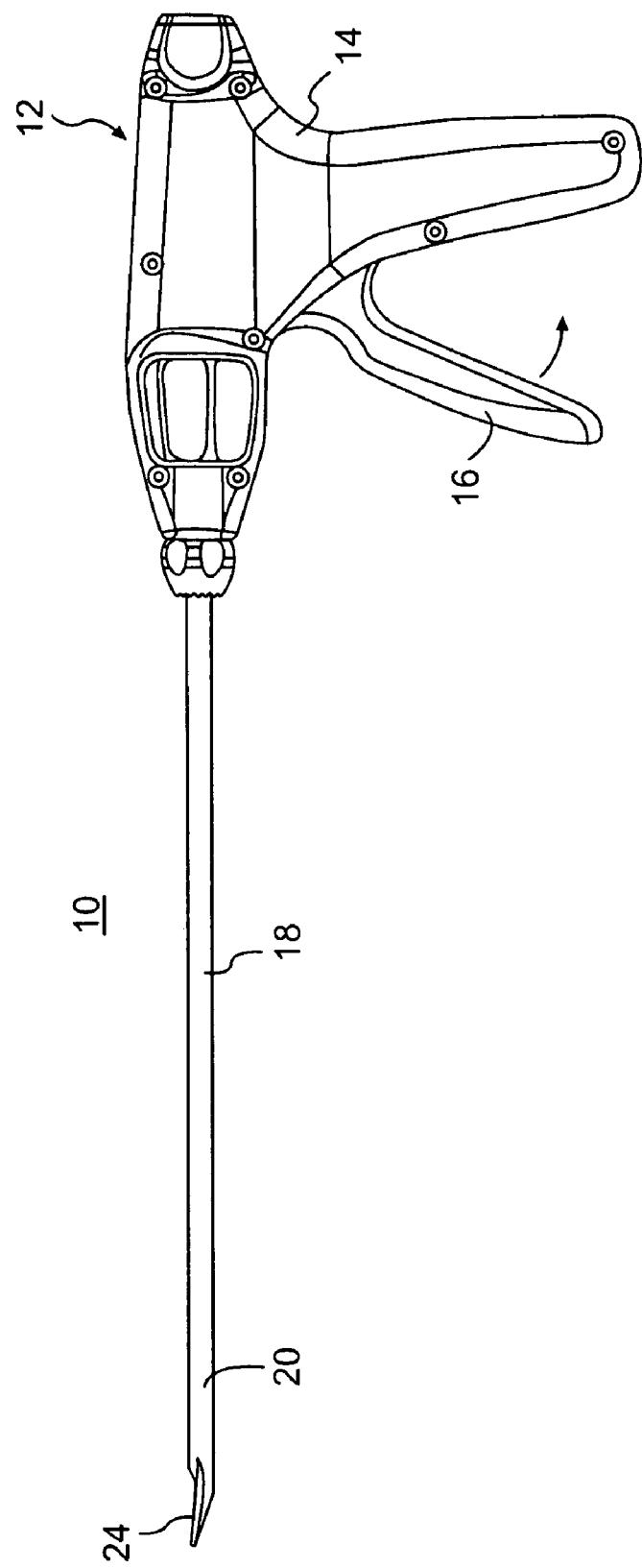
FIG. 1 is a side elevational view of a 5 millimeter clip applying arrangement showing the pistol like handle portion and the distal jaw configuration therewith.

Referring now to the drawings in detail, and particularly to FIG. 1, there is shown the present invention in which relates to an elongated medical clip applying device 10 having a first or proximal end 12 with a pistol like housing 14 having a trigger 16 therewith. The pistol like housing 14 holds and feeds an elongated cylindrically shaped delivery tube or barrel 18 having a distalmost end 20.

Figure 2:
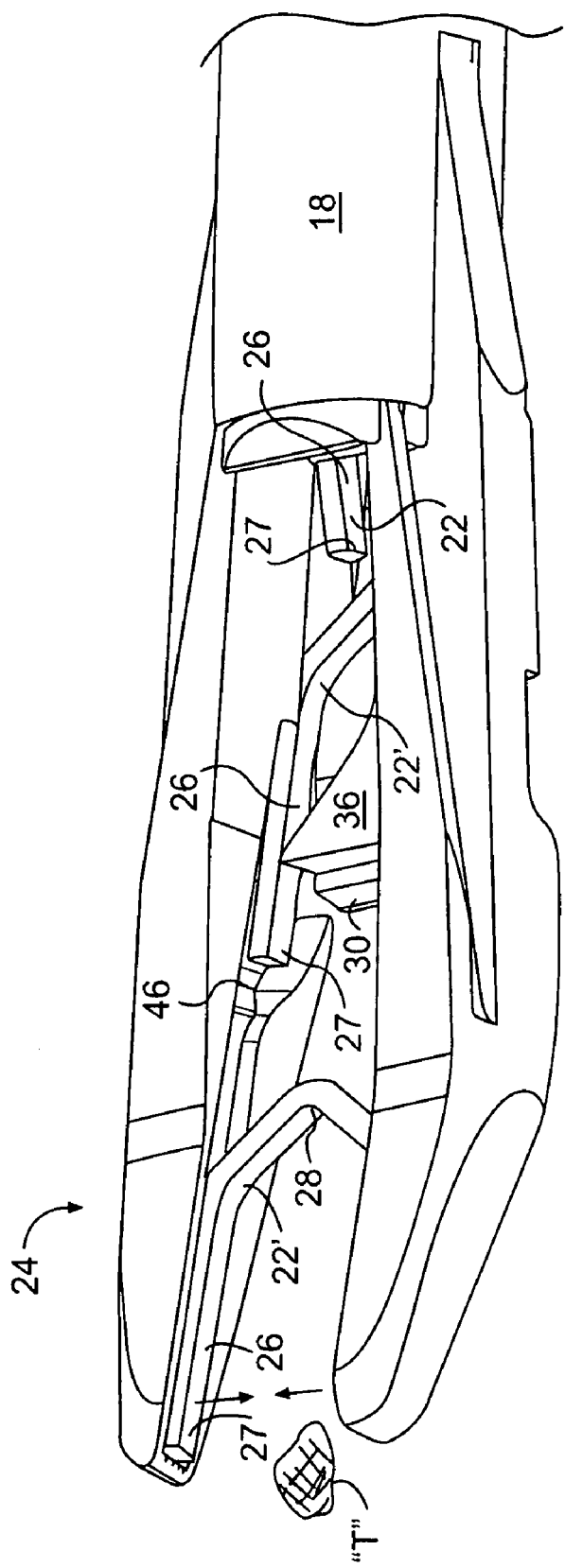
FIG. 2 is a perspective view of the jaws and an arrangement of clips being fed thereto.
Figure 3:
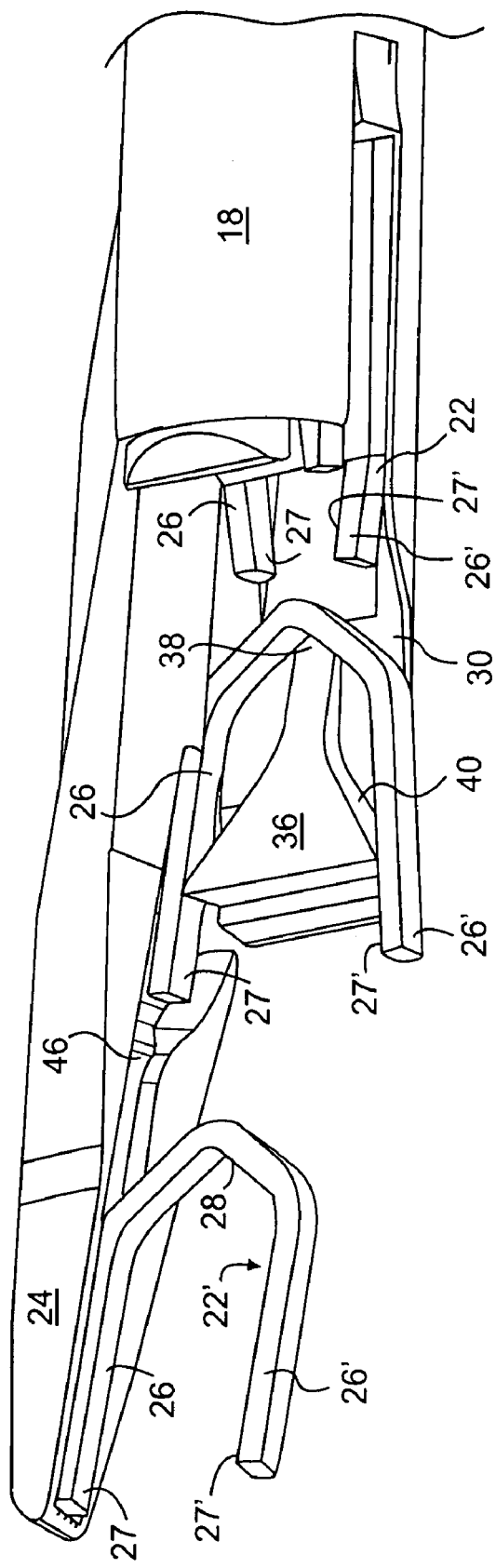
FIG. 3 is a view similar to FIG. 2 with portions cut away to show some more of the inner detail thereof.
Figure 4:
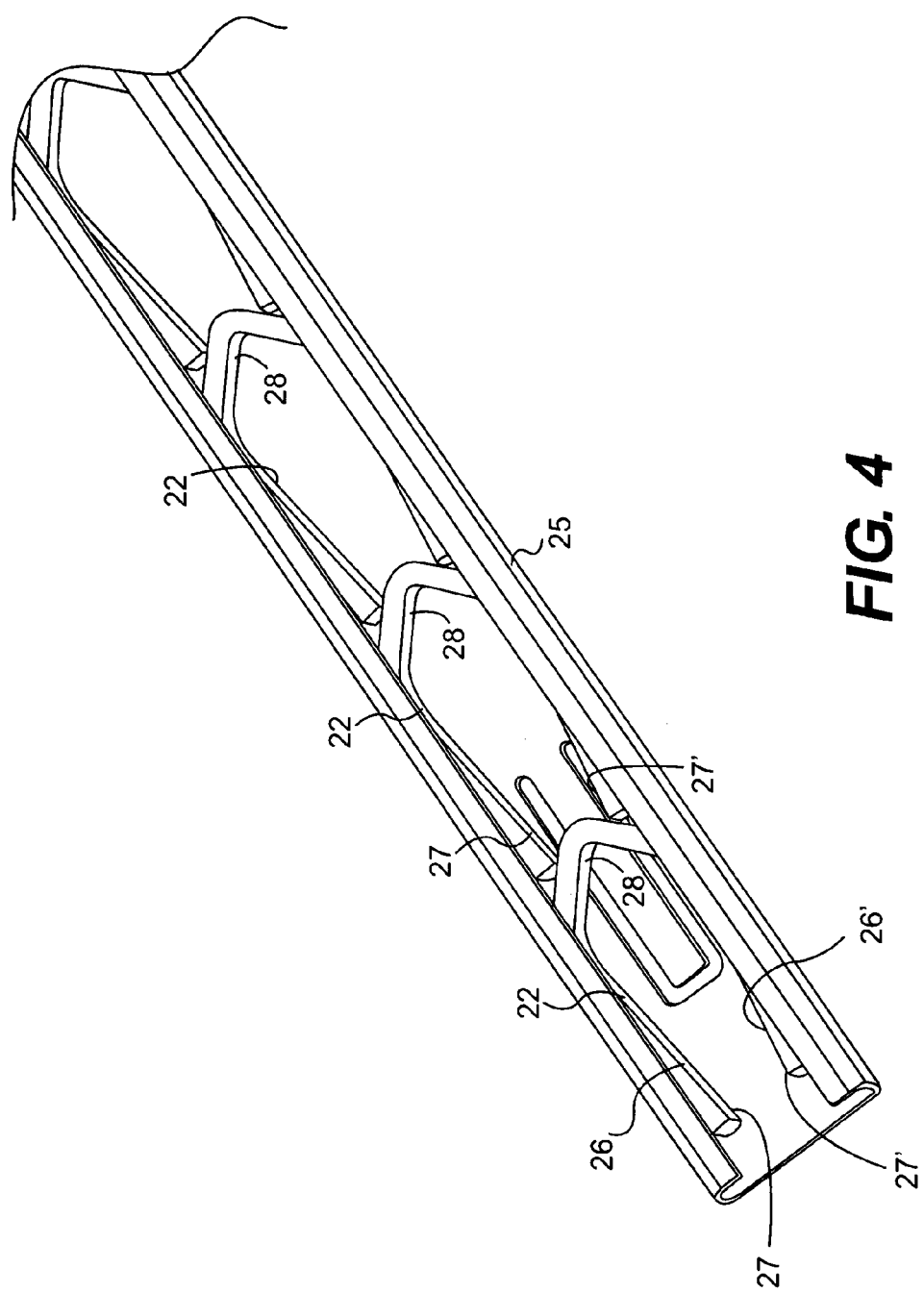
FIG. 4 is a perspective view of a 5 millimeter cartridge with a plurality of pre-formed clips arranged therewithin.

A plurality of pre-formed clips 22, as may be seen in FIGS. 2, 3, 4 and 7, are fed through the tube 18 towards a set of jaws 24 at the distalmost end 20 thereof. The clips 22 are introduced through a cartridge 25, as represented in FIG. 4. The cartridge 25 is inserted at the proximal end of the pistol-like housing 14 at the proximal end of the clip applier arrangement 10, as may be seen in my earlier co-pending U.S. patent application Ser. Nos. 10/085,737, filed 28 Feb. 2002, 09/934,378, filed 21 Aug. 2001 and 10/158,726 filed 30 May 2002 which are each incorporated herein by reference in their entirety.

The clips 22 of the present invention are fed through the barrel 18 the clip applying arrangement 10 in a five millimeter cartridge 24. Each cartridge 25, is similar to those shown in the aforementioned patent applications, except that the present invention of necessity, utilizes a narrower cartridge. The clips 22 utilized in the medical clip applying arrangement 10 of the present invention each comprise a pair of leg portions 26 and 26', connected by a V-shaped bridging portion 28, as seen in FIGS. 2, 3, 4, and 6, but best represented in FIG. 7. As the clips 22 reside and are pressed forward in the cartridge 25 by a bar feeder (not shown for clarity), they maintain their particular pre-formed configuration. That pre-formed configuration includes the legs 26 and 26' being non-parallel, that is, they are skewed at an angle of about 10 degrees with respect to their being parallel to one another, and their bridging portion 28 defining a V shape of about 75 to 90 degrees. As the pre-formed clips 22 advance down towards the distal end of the cartridge 25, (they are being pushed in a manner similar to that described in the aforementioned patent applications), they emerge from the distal end of the 5 millimeter tubular housing 18 between the handle 12 and the jaws 24 portion of the medical clip applier arrangement 10 as clips 22' with spread apart legs, ready for pinching a tissue "T".

Figure 5:
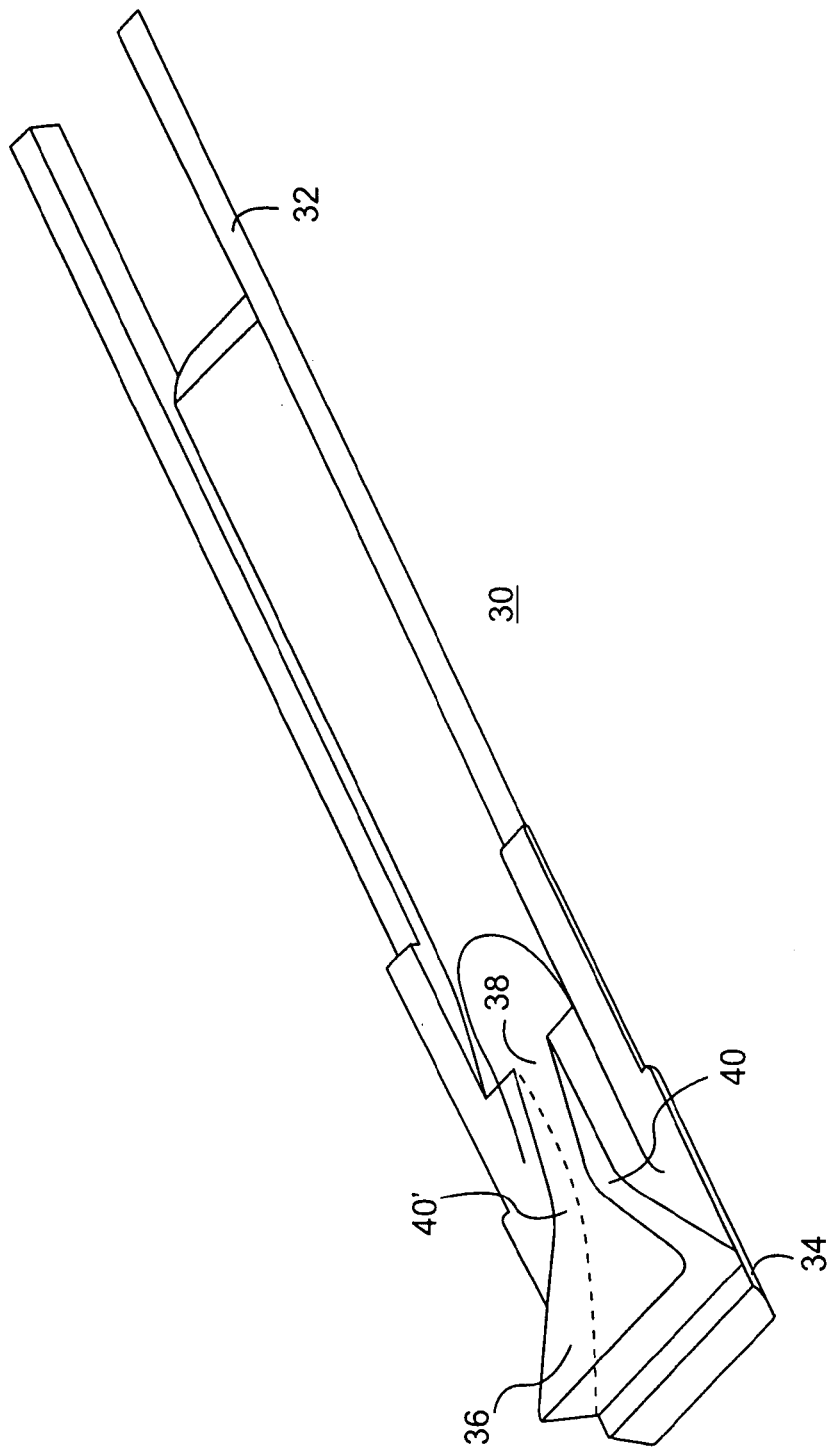
FIG. 5 is a perspective view of an elongated forming tool having a triangularly shaped forming component on a distal end thereof.
Figure 6:
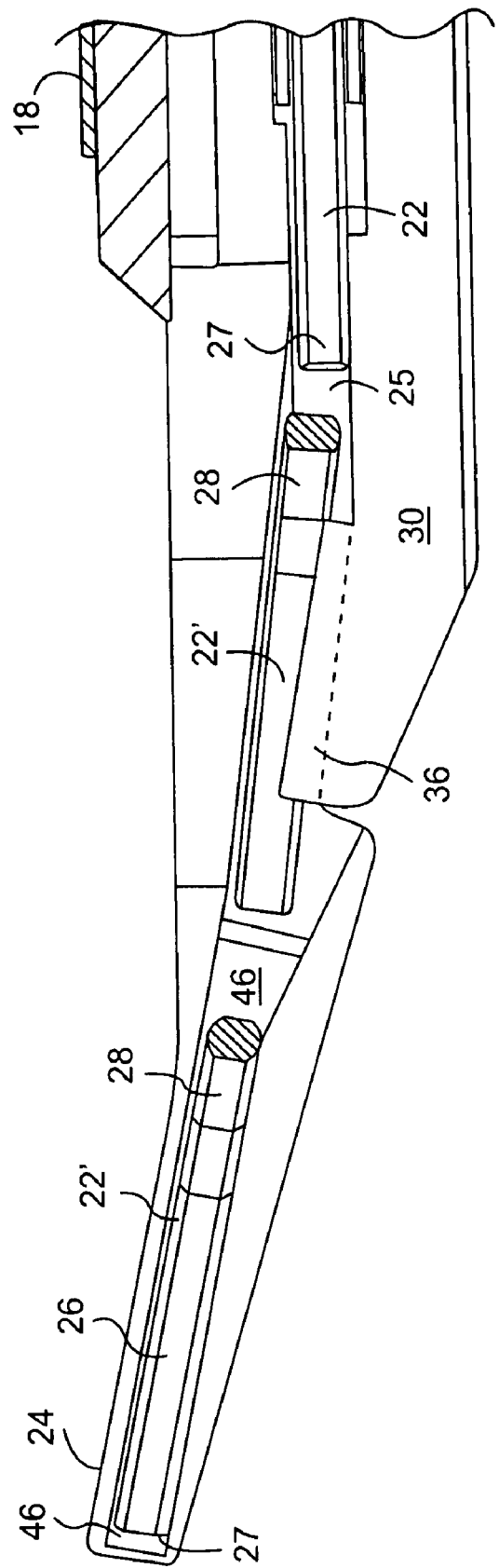
FIG. 6 is a cross sectional view of the distal end of the clip feeder arrangement showing the jaws and clips and portions of the forming tool arranged therewithin.

An elongated forming tool 30, shown by itself in FIG. 5, is disposed immediately adjacent the jaws 24 at the distal end 20 of the 5 millimeter tube 18, as is represented in FIGS. 2, 3 and 6. The elongated forming tool 30 includes a proximal planar bracket portion 32 having a distal end 34 with a triangularly shaped forming tool 36 thereon. The forming tool 36 has an apex 38 of one angle directed proximally towards the open end of the medical clips 22 in the cartridge 24, as is best shown in FIGS. 2 and 3. The triangularly shaped forming tool 36 has a pair of inclined surfaces 40 and 40' which define the sides of the triangular tool 36 and which engage the inner distalmost ends 27 and 27' of the legs 26 and 26' of the pre-formed clips 22, as shown in FIGS. 2 and 3, as the now widened-formed clips 22' become "wider" and advance distally. As the pre-formed clips 22 are each successively pushed distally, the sides 40 and 40' of the triangle 36 spread the legs 24 and 24' apart while simultaneously somewhat straightening out the V-shaped bridging portion 28 between those legs 26 and 26'. The distal end of those legs 26 and 26' of each successive clip 22 are caused to enter a channel 46 in each of the face portions of each respective jaw and are ready for pinching by those jaws 24 around mammalian tissue "T" within the human body. It is to be noted at this point that as the distal portion of the medical clip applier device is advanced into the abdominal area of a mammalian patient, those jaws 24 may be brought together to minimize their diameter and to keep them at that minimum diameter and in spacial conformance and alignment with the 5 millimeter tubular housing 18 from which they extend. Once inside the patient, however, the jaws 24 may be opened to receive the net now spread apart leg portions 26 and 26' of the newly formed (legs now spread further apart and bridge portion staigneened somwhat, and no longer "pre"-formed) clips within the body of the patient being operated upon.

Figure 7:
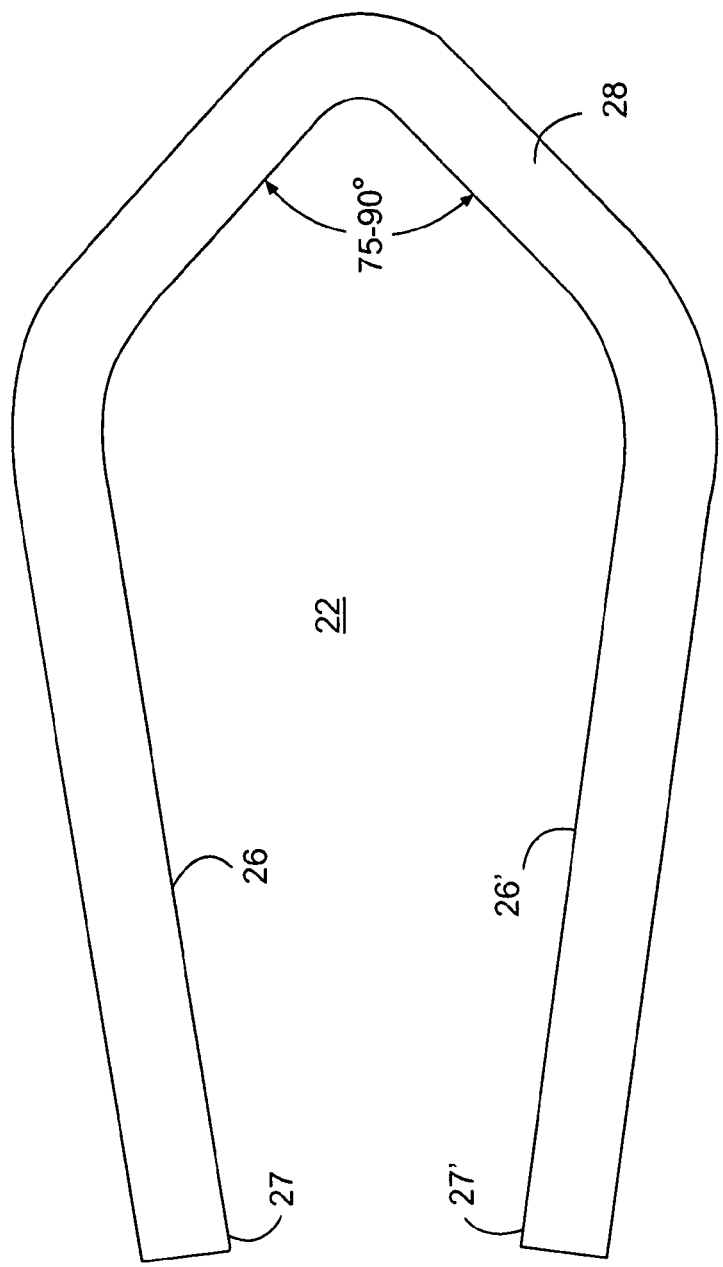
FIG. 7 is a planned view of a 5 millimeter pre-formed clip.
Figure 8:
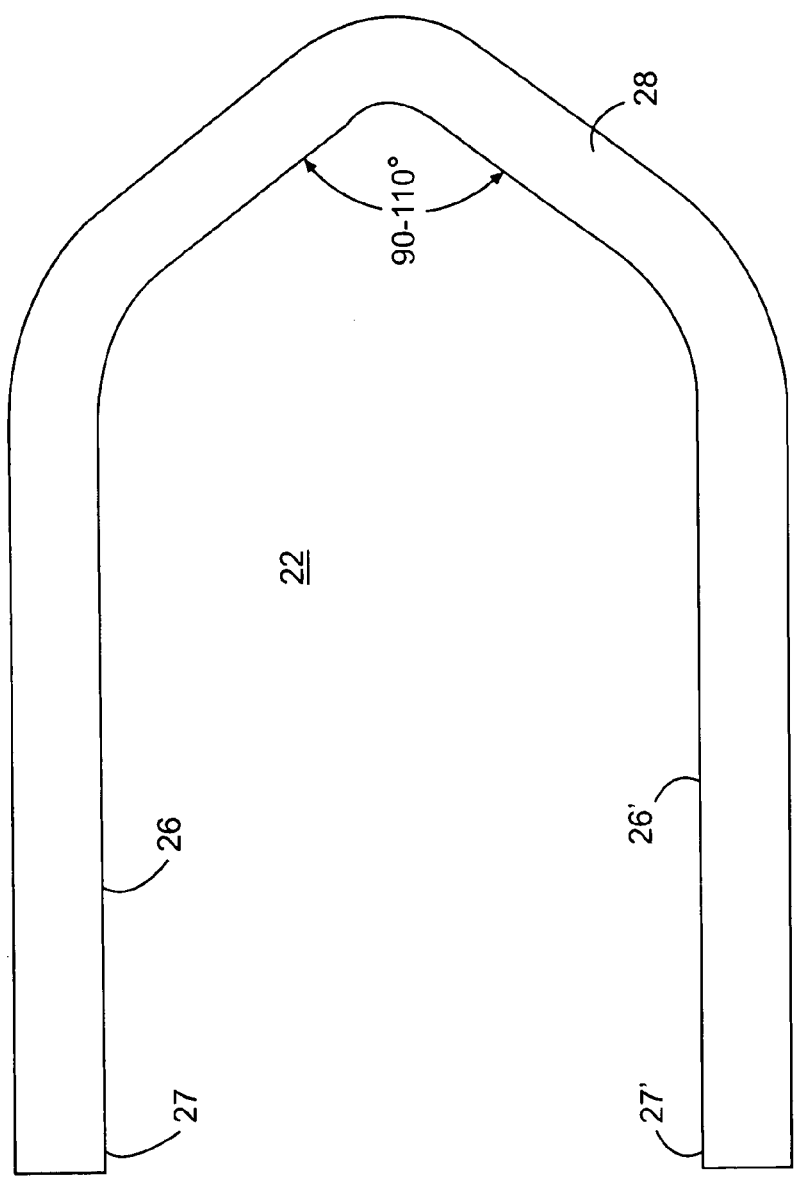
FIG. 8 is a planned view of a 5 millimeter un-"pre" formed clip after it has been manipulated by the forming tool adjacent the jaws of the medical clip applying device.

Thus what has been shown is the utilization of a pre-formed clip 22 having a leg spread dimension of no more than 5 millimeters being successively advanced along a feed cartridge 25 within a 5 millimeter diameter barrel housing 18 and upon emersion from the distal end 20 of that housing, the legs 26 and 26' of that pre-formed clip 22, going from a somewhat slightly pinched configuration and from its bridging portion 28 being of a 75 to 90 degree V-configuration, preferably about 82 degrees, as represented in FIG. 7 to a configuration represented in FIG. 8, where the legs 26 and 26' are generally parallel by virtue of the bridging portion 28 now being somewhat straightened (out to an angle of generally about 90 to 110 degrees-preferably about 100 degrees) and thus spreading the separation of the outer sides those legs 26 and 26' out an increased or "delta" amount of about 5 millimeters to approximately 10 millimeters, which is generally the standard dimension of a standard clip, as represented as clip 22' in FIG. 8. Upon reaching the distalmost end of the channel 46 within the pinching jaws 24, those jaws 24 are effected, to pinch together the clip 22 along portions of a tissue "T" of a patient, to effect the pinched clip's purpose. Withdrawal of the medical clip applying device 10 through the smaller operative laparoscopic opening is permitted, by the squeezing together of the jaws 24 to the same overall diametric dimension as the elongated tubular housing 18 enclosing the 5 millimeter cartridge 25 which supplies the pre-formed clips 22 therethrough.

Thus a narrow pre-formed clip of substandard dimensions is permitted to be delivered into a mammalian body and expanded within that mammalian body prior to its being pinched about tissue within that mammalian body by a narrow diameter delivery arrangement which thus minimizes the trauma to the patient and minimizes that patient's healing time.

We claim:

1. A clip applying device for the insertion and pinching of a medical clip within a mammalian body portion, comprising:
    a housing supporting a proximal end of a delivery tube of said device;
    a pair of pinchable jaws movably arranged at a distal end of said delivery tube, said pinchable jaws configured to accept a pre-formed wire-like clip having leg portions, said leg portions having a first width between said leg portions, said wire-like clip being movably disposed within said delivery tube between said housing and said jaws; and
    a tool adjacent said jaws arranged to enlarge said clip from said first width to a wider second width, as said clip emerges from said delivery tube.

2. The clip applying device as recited in claim 1, wherein said tool comprises a triangular form arranged to frictionally engage said leg portions of said clip to bias them apart.

3. The clip applying device as recited in claim 1, wherein said clip has a pre-formed bridging portion connecting said leg portions, said bridging portion being of a "V" configuration.

4. The clip applying device as recited in claim 3, wherein said pre-formed bridging portion of said clip at the first width, comprises an angle of about 75 to 90 degrees.

5. The clip applying device as recited in claim 3, wherein said bridging portion of said clip at the second width, comprises an angle of about 90 to 110 degrees.

6. The clip applying device as recited in claim 1, wherein said leg portions are skewed with respect to one another.

7. The clip applying device as recited in claim 1, wherein said delivery tube has an outer diameter of about 5 millimeters.

8. The clip applying device as recited in claim 1, wherein said leg portions of said clip at the second width are parallel.

9. The clip applying device as recited in claim 1, further comprising a cartridge configured to be loaded with said pre-formed clip, said cartridge being removably insertable into said delivery tube at a proximal end of said delivery tube.

10. A method of introducing a medical clip into a mammalian patient, comprising:
    providing a pre-formed wire-like clip into a delivery tube, the wire-like clip having leg portions and a bridging portion connecting said leg portions, the wire-like clip having a first width between the leg portions, said delivery tube having a pair of clip pinching jaws on a distal end thereof configured to accept the wire-like clip;
    inserting the delivery tube into the patient body;
    advancing said clip through said tube and towards said jaws;

widening said clip into a second width prior to pinching thereof; and squeezing said clip widened into the second width to pinch, by the jaws, a tissue of said patient.

11. The method as recited in claim 10, wherein said widening comprises forming said leg portions of said clip in a parallel relationship.

12. The method as recited in claim 11, wherein said widening further comprises engaging said leg portions of said clip by a forming tool so as to form said leg portions thereof into said parallel relationship.

13. The method as recited in claim 10, wherein said widening comprises forming said bridging portion of said clip into a wider angled "V" shape.

14. The method as recited in claim 10, wherein said squeezing comprises squeezing said jaws together to permit said device to be removed from said patient through a 5 millimeter opening in said patient.

15. The method as recited in claim 10, wherein said providing a pre-formed wire-like clip into a delivery tube comprises:

providing the clip within a removable cartridge; and inserting the cartridge into a delivery tube at a proximal end of the delivery tube.

16. A method of introducing a narrow clip into a patient and pinching tissue within said patient by a wider clip widened from the narrow clip once within said patient, said method comprising:

introducing a delivery tube into a patient, said tube having a pre-formed wire-like clip forming a narrow first width;

widening said pre-formed wire-like clip into a second wider width upon advancement of said wire-like clip from said tube; and pinching said widened wire-like clip by a pair of squeezable jaws arranged about tissue upon said clip being widened.

17. The method as recited in claim 16, further comprising:

forming a bridging portion that connects leg portions of said clip from a 75 to 90 degree bend therein into a 90 to 110 degree bend to thus widen and spread apart said leg portions of said pre-formed clip.

18. The method as recited in claim 16, wherein said widening comprises widening a bridge portion that connects leg portions of said clip, by a forming tool, prior to said pinching of said clip.

19. The method as recited in claim 18, wherein said widening a bridge portion comprises sliding a distal end of each of a pair of legs of said clip on an edge of said forming tool to effect said widening of said bridge portion of said clip.

20. The method as recited in claim 16, wherein said widening of said pre-formed clip comprises spreading the leg portions of said clip apart.

21. The method as recited in claim 16, further comprising:

providing the pre-formed wire-like clip within a removable cartridge; and inserting the into said delivery tube at a proximal end of the delivery tube.

22. A method of introducing a narrow clip into a patient and pinching tissue within said patient by a wider clip widened from the narrow clip within said patient, said method comprising:

introducing a delivery tube into a patient, said tube provided with squeezable jaws and a pre-formed wire-like clip forming a narrow first width;

widening said pre-formed wire-like clip to form a second wider width upon advancement of said clip from said tube so as to be able to engage tissue and pinch said tissue with said widened clip; and pinching said widened wire-like clip by the squeezable jaws.

23. The method as recited in claim 22, wherein said widening said pre-formed wire-like clip is performed within said patient.

24. The method as recited in claim 22, further comprising:

providing the pre-formed wire-like clip within a removable cartridge; and inserting the into said delivery tube at a proximal end of the delivery tube.

* * * * *